United States Patent [19]

Newman et al.

[11] Patent Number: 4,804,443

[45] Date of Patent: Feb. 14, 1989

[54] METHOD AND APPARATUS FOR THE DETERMINATION OF ELECTROCHEMICALLY ACTIVE COMPONENTS IN A PROCESS STREAM

[75] Inventors: Oliver M. G. Newman, Moonah; Alan M. Bond, Toorak; Robert W. Knight, Geelong, all of Australia

[73] Assignee: Electrolytic Zinc Company of Australia Limited, Melbourne, Australia

[21] Appl. No.: 76,485

[22] Filed: Jul. 22, 1987

[30] Foreign Application Priority Data

Apr. 13, 1987 [AU] Australia ................. PI1386

[51] Int. Cl.⁴ ........................................... G01N 27/42
[52] U.S. Cl. ................................... 204/1 T; 204/406; 204/409; 204/411; 204/412; 204/413
[58] Field of Search ............... 204/1 T, 413, 406, 411, 204/412, 409

[56] References Cited

U.S. PATENT DOCUMENTS 4,220,515 9/1980 de Kreuk ................ 204/413 X

FOREIGN PATENT DOCUMENTS 2017920 10/1979 United Kingdom .

OTHER PUBLICATIONS

M. D. Booth et al., Talanta, vol. 17, No. 11, pp. 1059–1065 (1970).
A. M. Bond et al., "Simultaneous Determination of Cadmium, Cobalt, Copper", etc., *Journal of Liquid Chromatography* 6(10), pp. 1799–1822 (1983).
A. M. Bond et al., "Development of a Microprocessor Based Electrochemical Instrument", etc., *Analytica Chimica Acta*, 165, pp. 209–216 (1984).
A. M. Bond et al., "High Flow-Rate Cells for Continuous Monitoring of Low Concentrations of Electroactive Species", etc., *Analytica Chimica Acta*, 127, pp. 121–133 (1981).
Edwin S. Pilkington et al., "Determination of Trace Elements in Zinc Plate Electrolyte by Differential Pulses Polarography", etc. Analytical Chemistry, vol. 48, pp. 1665–1669 (1976).
A. M. Bond et al., "Comparative Study of a Wide Variety of Polarographic Techniques with Multifunctional Instrumentation", *Analytical Chemistry*, vol. 44, pp. 721–731 (1972).
A. M. Bond et al., "Direct Current, Alternating Current, Rapid and Inverse Polarographic Methods for Determination of Tin (IV)", Analytical Chemistry, vol. 42, pp. 1165–1168 (1970).
A. M. Bond, "Modern Polarographic Methods in Analytical Chemistry", Chap. 9, Stripping Voltammetry, pp. 435–472.

*Primary Examiner*—G. L. Kaplan
*Attorney, Agent, or Firm*—Finnegan, Henderson, Farabow, Garrett & Dunner

[57] ABSTRACT

A method and apparatus for determining electrochemically active components in a process stream. The method comprises the steps of providing a sample in which the components are contained, and depositing the components onto a working electrode, altering the environment of the working electrode so that it is immersed in a supporting electrolyte by effecting a matrix exchange and stripping the deposited electrochemically active components from the working electrode into the supporting electrolyte. The method and apparatus utilize a measurement cell which comprises a vessel (10) for containing the supporting electrolyte and a mercury drop electrode (150). A flow injector (16) is used to inject a flow of a sample electrolyte which contains the electrochemically active component; and into the vessel so that the sample electrolyte surrounds the mercury drop electrode and then sinks away from the mercury drop electrode (150) to the bottom of the vessel where it is removed via an outlet (20) to thereby leave the mercury electrode (150) immersed in the supporting electrolyte. The deposited impurities are stripped from the working electrode using variable time domain transient electrochemical stripping voltammetry. The sequence of steps including the deposition of the impurities from an injected flow of electrolyte sample are repeated under microprocessor control (50).

14 Claims, 3 Drawing Sheets

METHOD AND APPARATUS FOR THE DETERMINATION OF ELECTROCHEMICALLY ACTIVE COMPONENTS IN A PROCESS STREAM

This invention relates to a method and apparatus for the determination of electrochemically active components in a process stream and in particular to the determination of impurities in an electrolyte.

The presence of impurities at unacceptably high levels in zinc plant electrolytes can result in both inefficient utilisation of electrical power during electrolysis (e.g. caused by copper, and antimony) and the contamination of the product zinc (e.g. with lead, cadmium and thallium). When impurities exceed established threshold levels, electrolyte purification procedures must be adjusted to increase the efficiency of impurity removal. For instance, inefficient removal of copper and cadmium can be rectified by adjusting a purification step which precedes electrolysis and involves the removal of copper and cadmium from solution by cementation (i.e. metal displacement) onto zinc dust. It is important to monitor regularly the zinc plant electrolyte in order to optimise both the efficiency of the electrolysis step (i.e. minimum consumption of electrical power) and the purification step (minimum reagent consumption). In some instances it may be desirable to monitor the solution ahead of the purification step in order to achieve the latter objective.

Impurities can create difficulties during zinc electrolysis when present at concentrations as low as $10^{-9}$ times the concentrations of zinc. In the case of zinc sulphate electrolytes the ratio of an impurity concentration to the host zinc concentration is often of the order of 1 to $10^7$ in the purified electrolyte compared with ratios as low as 1 to 10 in unpurified electrolyte.

The large concentration difference between zinc and the impurities precludes the successful application of many analytical techniques. Presently used spectrographic, complexometric methods and some electrochemical techniques frequently require extensive sample pretreatment to determine low impurity levels. Consequently most analytical determinations are made off-line in a conventional laboratory situation.

Thus, prior art systems are labour intensive and require considerable supervision by skilled personnel in order to determine impurity concentrations in electrolytes. Furthermore, conventional techniques are impaired by interference caused by high concentrations of other species being present with the impurities. If interference is expected in conventional techniques, it is often necessary to alter the electrolyte by the addition of suitable substances to avoid interference.

The object of the present invention is to provide a method and apparatus for determination of electrochemically active components in process streams which overcomes the above drawbacks.

The invention may be said to reside in a method for the determination of electrochemically active components in process streams comprising the steps of depositing the electrochemically active component onto a working electrode from an electrolyte sample which includes said electrochemically active component, altering the environment of the working electrode so that it is immersed in a supporting electrolyte by effecting a matrix exchange and stripping the deposited electrochemically active component from the working electrode into the supporting electrolyte.

The invention may also be said to reside in an apparatus for the determination of electrochemically active components in a process stream comprising a measurement cell containing an electrode system which comprises a working electrode, reference electrode and an auxiliary electrode, means for conveying a sample solution containing said component to said working electrode, means for energizing said working electrode so that said components are deposited thereon, means for changing the environment in which the working electrode is immersed so as to effect a matrix exchange so that the working electrode is immersed in a supporting electrolyte and means for again energizing said working electrode to strip the deposited components from said working electrode into said supporting electrolyte.

Since the present invention utilizes the combination of a matrix exchange between a sample electrolyte in which deposition takes place and a supporting electrolyte in which stripping takes place, a suitable supporting electrolyte can be chosen which avoids interference and also the method and apparatus lends itself to automation which can be microprocessor controlled and therefore the amount of labour or supervision which is required is greatly reduced. The fact that the system can be automated enables continual monitoring of a process stream to determine the concentration of an electrochemically active component in that stream for considerable periods of time, for instance of several days or weeks with little or no intervention required from skilled operators.

Preferably, the alteration of the environment in which the electrode system is immersed to effect a matrix exchange is performed by immersing the electrode system in the supporting electrolyte which is less dense than the sample electrolyte, injecting a flow of the sample electrolyte onto said working electrode and stopping the flow of injected sample electrolyte so that the same electrolyte sinks away from the working electrode to leave the electrode system in an environment comprised of the supporting electrolyte.

Preferably, the working electrode is a mercury electrode which may be in the form of a hanging mercury drop electrode, a static mercury drop electrode or a mercury film electrode.

A further aspect of the invention may be said to reside in a method for the determination of impurities in electrolytes containing a much higher concentration of another electrochemically active species characterised by the automated and continual performance of a series of sequential steps which are repeated under microprocessor control, said sequence of steps including the deposition of said impurities from an injected flow of electrolyte sample containing the impurities onto a mercury electrode immersed in a supporting electrolyte which is less dense than the sample electrolyte, stopping the flow of injected electrolyte and finally effecting a matrix exchange by stripping the deposited impurities from the mercury electrode into the less dense supporting electrolyte using variable time domain transient electrochemical stripping voltammetry.

The invention may also be said to reside in an apparatus for the determination of impurities in electrolyte containing a much higher concentration of another electrochemically active species characterized by a measurement cell for containing a supporting electrolyte, means for forming a mercury electrode to be immersed in said supporting electrolyte, means for injecting a flow of a sample electrolyte containing said impurities onto said mercury electrode, means for stopping the flow of injected sample electrolyte to effect a matrix exchange whereby the mercury electrode is surrounded by said supporting electrolyte, means for energizing said mercury electrode so as to strip the deposited impurities from the mercury electrode in the supporting electrolyte using variable time domain transient electrochemical stripping voltammetry and wherein microprocessor control means is provided for automating the injection means, the stopping means and the energizing means, so that they occur in sequence.

The use of a stopped flow injection procedure under microprocessor control allows the temporal separation of the sequential steps of, firstly depositing the impurities onto the mercury electrode, and secondly stripping the deposited impurities into an appropriate supporting electrolyte. This temporal separation of the two steps effects the matrix exchange of the impurities from the sample electrolyte into the supporting electrolyte. Therefore, the method and apparatus lends itself to automation whereby continual monitoring of a chemical process plant can take place for days or even weeks without manual intervention.

The preferred embodiment of the invention may also include the removal of excess of the said another electrochemically active species prior to the sample electrolyte containing that species being injected onto said electrode. This step is particularly preferred when determining concentrations of nickel or cobalt in a zinc recovery plant so as to remove excess zinc before impurity measurement takes place. Removal of excess of the another electrochemically active species may take place by cationic exchange techniques or by making the solution alkaline and precipitating the species from the solution.

In the preferred embodiment of the invention the method takes place in a measurement cell which includes said mercury electrode, a flow injecting nozzle for injecting a flow of the sample solution onto the mercury electrode, an outlet arranged at the bottom of the cell for removing sample solution from said cell and means for introducing supporting electrolyte into said cell whereby when the flow of sample solution is stopped, sample solution sinks to the bottom of the cell and is removed from the cell via the outlet. The sample solution may be removed from the bottom of said cell through the said outlet by draining, pumping, siphon action, or by an overflow pipe coming from near the base of the cell.

Preferably the cell also has an outlet for draining off excess mercury which sinks to the bottom of the cell.

The variable time domain transient electrochemical striping voltammetry may be differential pulse anodic stripping voltammetry having a pulse which is in the range of 1 to 400 milliseconds to strip the impurities into the supporting electrolyte. Most preferably the pulse width is in the range 1 to 40 milliseconds. In an alternative embodiment linear sweep stripping voltammetry may be employed. Operation with short differential pulse widths increases the sensitivity and selectivity with which impurities are determined, which in turn allow the deposition time in the measurement cycle to be decreased. Since deposition time may be the dominant component of the measurement cycle a decrease in the deposition time decreases the measurement cycle and increases the frequency with which a process can be monitored by the method of the invention. Thus, the efficiency of on-line surveillance of the process can be increased.

Preferably the impurities comprise one or more of the group of elements comprising cadmium, copper, lead, antimony, thallium, nickel, cobalt, arsenic, tin and germanium and the electrochemically active species present at a much higher concentration is zinc, which is present as a sulphate electrolyte. The supporting electrolyte depends on the impurities it is desired to determine, and the concentrations of the impurities.

Preferably the impurity/supporting electrolyte choices are:

| Impurity | Supporting electrolyte |
| --- | --- |
| cadmium, lead, thallium | Chloride solution |
| copper, antimony | Nitrate solution |
| nickel, cobalt | Ammonium/ammonium chloride solution buffered at pH of about 8. |

Preferably the chloride solution has a concentration in the range 0.1 to 4.0 molar, and most preferably in the range 0.75 to 2.0 molar. Preferably when copper and antimony are simultaneously present the supporting electrolyte is a nitrate solution having a concentration in the range 0.1 to 4.0 molar and most preferably in the range 0.75 to 2.0 molar containing minimal amounts of chloride.

The preferred method of determining the extended impurity set cadmium, copper, lead, antimony, and thallium is to conduct a first measurement cycle in chloride supporting electrolyte in which the components cadmium, lead, and thallium are determined during the stripping cycle, followed by a second measurement cycle in which the supporting electrolyte is a nitrate solution and the components copper and antimony are determined during the stripping cycle. The two measurement cycles can either be conducted in a separate measurement cell, which may be under the control of a single microprocessor and data acquisition system or in the same cell with the supporting electrolyte changed between measurement cycles.

In another embodiment of the invention the sample electrolyte is zinc sulphate and the aforementioned impurities vary widely in concentration between sequential samples. In this embodiment the sensitivity of the determination of adjusted automatically by the microprocessor, which alters appropriate parameters of the measurement cycle. For instance, if there is a major increase in the concentration of an impurity between sequential samples the microprocessor can decrease the length of the period of flow injection and thus decrease the amount of impurity which is deposited onto the mercury drop. Thus the amount of impurity subsequently stripped into the supporting electrolyte is decreased, such that it lies within the range of the pre-calibrated stripping voltammetric technique. It is obvious to one skilled in the art that a standard sample can be periodically injected into the measurement system to check the calibration. The microprocessor is programmed to effect re-calibration and measurement range adjustment automatically.

A further aspect of the invention may be said to reside in a measurement cell comprising a vessel for containing a supporting electrolyte, means for supporting an electrode system in said vessel so that the electrode system is immersed in the supporting electrolyte, flow injector means for injecting a flow of sample electrolyte into said vessel and onto the working electrode when supported in said veseel, an outlet at the bottom of said vessel, wherein said sample electrolyte is periodically injected into said vessel and sinks to the bottom of said vessel where it is removed from the vessel via said outlet and means for introducing supporting electrolyte into said vessel to replace electrolyte removed from said veseel.

A preferred embodiment of the invention will be described with reference to the following examples and the accompanying drawings. In the drawings.

Figure 1:
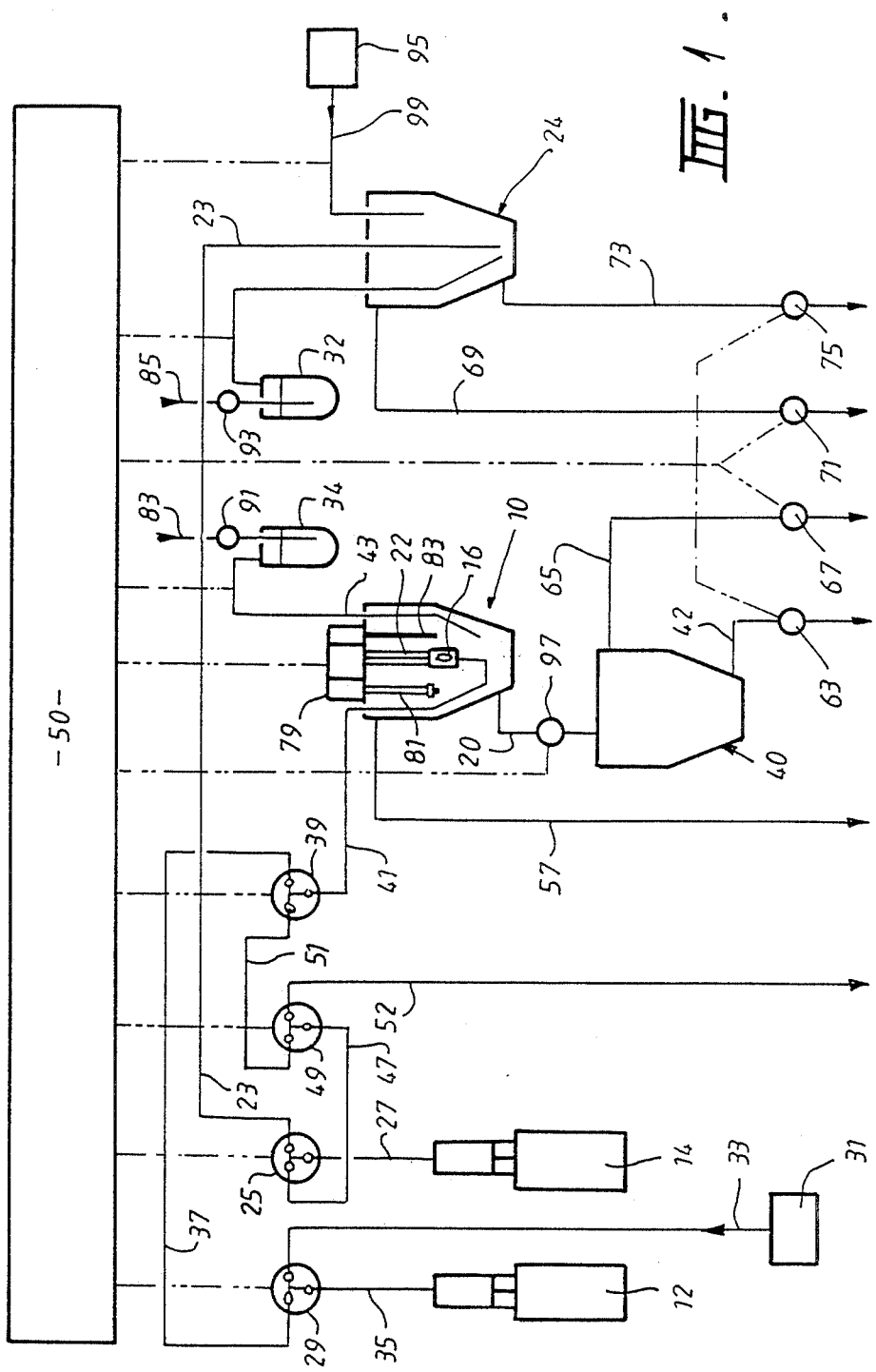
FIG. 1 is a schematic diagram of an apparatus for carrying out the preferred method of the invention.
Figure 2:
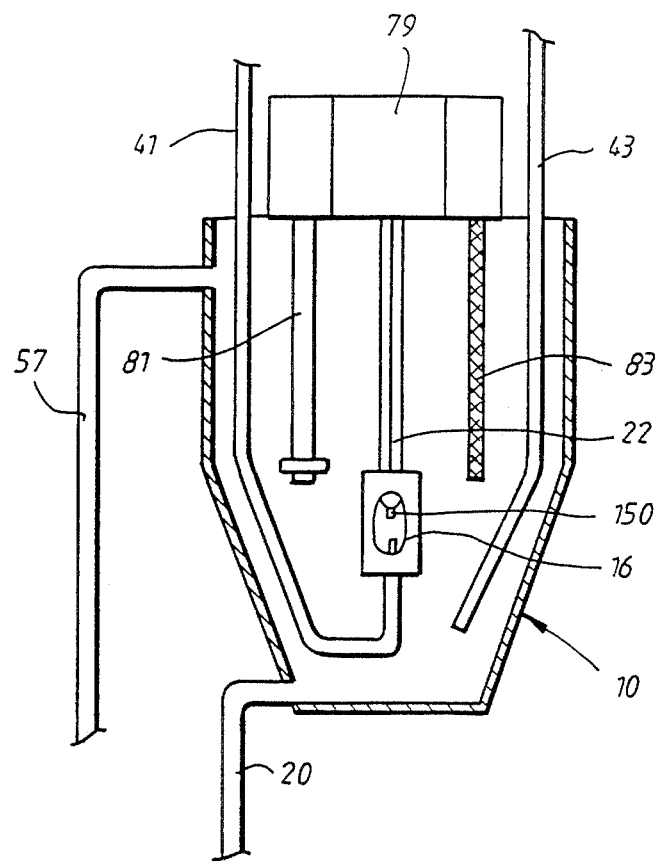
FIG. 2 is a detailed view showing part of the apparatus of FIG. 1.

With reference to the drawings an apparatus embodying the invention is shown in which a measurement cell 10, which generally comprises a suitable vessel, receives supporting electrolyte from an automated supporting electrolyte burette 12. The flow of supporting electrolyte is controlled by the automated burette and is introduced into the measurement cell 10. An automated sample burette 14 which receives a sample solution from a zinc processing plant supplies sample electrolyte to a flow nozzle 16 which is arranged in the cell 10. The flow of the sample solution is controlled by the automated burette 14. The flow nozzle is preferably a Princeton Applied Research flow nozzle disclosed in British patent specification No. 2017920. The measurement cell 10 has an outlet 20 arranged at the bottom part of the cell. A support member 22 is provided for supporting a mercury electrode 150 such as a mercury drop electrode in the vessel 10. Preferably the mercury drop 150 which forms the of mercury to replenish continually the mercury drop electrode. Preferably the mercury drop 150 which forms the working electrode is made as small as possible to increase stability when suspended from support 22 which may be a glass capillary. This preferred aspect of the invention is important when the invention is used in an industrial environment in which equipment is subject to a high level of vibration. Sample electrolyte is supplied to vessel 24 from a remote sampling system. The sample electrolyte is purged in the vessel 24 prior to extraction into burette 14 for supply to cell 10. The supporting electrolyte contained in cell 10 is purged prior to analysis with nitrogen. The nitrogen used to purge vesesl 24 and cell 10 is independently washed in vessels 32 and 34 respectively before use.

Supporting electrolyte is provided from burette 12 into the cell 10 so that the mercury electrode is immersed in the supporting electrolyte. The sample electrolyte containing impurities may then be provided from the burette 14 to the flow nozzle 16 and injected onto the mercury electrode 150. Under microprocessor control the mercury electrode 150 is energized so that the impurities in the sample electrolyte are deposited on the mercury drop electrode. Under microprocessor control the flow of sample electrolyte is stopped by appropriate control of the automated burette and the sample solution sinks to the bottom of the vessel due to the difference in density between the sample solution and the supporting electrolyte. The mercury electrode with the deposited impurities thereon is therefore immersed in the supporting electrolyte and matrix exchange is therefore effected so that the electrode system is immersed in a supporting electrolyte in which impurity concentration can be determined without interference. Under microprocessor control the mercury electrode supported by the support 22 is energized by applying a potential to the electrode system to effect time domain transient electrochemical stripping of the impurities from the mercury electrode supported by support 22 and by microprocessor monitoring of the output current the amount of impurities in the electrolyte sample can be determined and therefore the amount of impurities in the zinc processing plant sample can be determined. Preferably the amount of impurities is determined by producing a graph of current versus applied voltage and measuring peak currents or peak current areas to determine the impurity concentration.

Sample electrolyte is drained from the bottom of the vessel 10 together with a limited amount of supporting electrolyte via the outlet 20 and passes through the vessel 40 in which mercury is collected. An outlet 42 may be provided in the vessel 40 for draining mercury from the bottom of the vessel as mercury collects in the bottom of the vessel. The mercury may be collected in a suitable vessel (not shown).

The following table shows specific gravity of typical zinc plant electrolyte and supporting electrolytes.

TABLE 1

| Specific Gravities of Typical Zinc Plant Electrolyte and Supporting Electrolytes | | | |
|---|---|---|---|
| | Solution | Molarity | Specific Gravity at 20° C. |
| | Zinc Plant Electrolyte | — | 1.25 to 1.5 |
| SUPPORTING ELECTROLYTES | KCl | 3.742 | 1.16 |
| | | 1.053 | 1.05 |
| | KNO$_3$ | 2.759 | 1.16 |
| | | 1.051 | 1.07 |
| | NaCl | 3.270 | 1.13 |
| | | 1.032 | 1.04 |
| | NaNO$_3$ | 3.318 | 1.18 |
| | | 1.123 | 1.06 |

Figure 3:
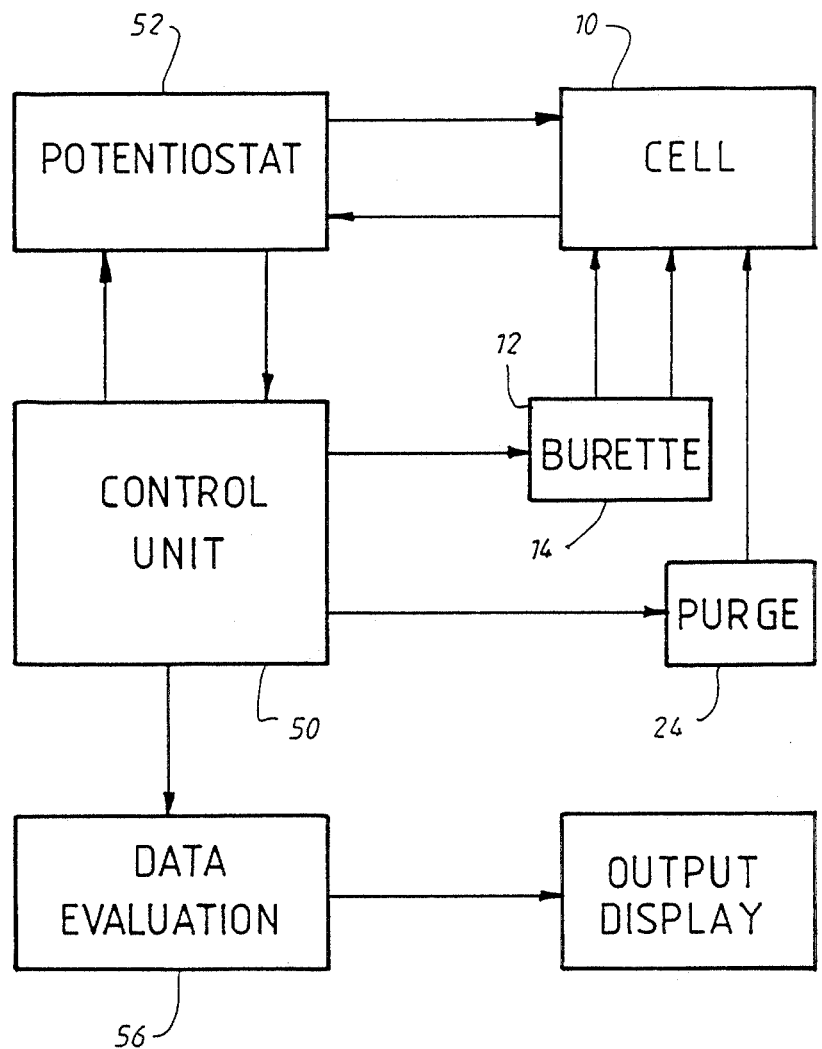
FIG. 3 is a schematic diagram showing the preferred method and apparatus of the invention.

With reference to FIG. 3, a block diagram showing the system of the preferred embodiment is given. A control unit 50 which may comprise a master-slave dual microcomputer arrangement (such as a Sphere 6809 microprocessor system or an Apple 2e microcomputer and Motorolla MEK-6800-D2 microprocessor system). However, a single integrated microcomputer system could be utilized. A potentiostatic control unit 52 is coupled to the control unit 50. The potentiostatic control may be achieved with an E611 VA detector made by Metrohm AG, (Herisau, Switzerland). The control unit 50 controls burettes 12 and 14 which are utilized to deliver the supporting electrolyte and sample electrolyte to the vessel 10. The sample electrolyte, supporting electrolyte and cell solutions were continually purged with nitrogen from the nitrogen purge vessels under the control of the control unit 50.

A preferred operating sequence will be described with reference to FIG. 1. It should be understood that the time limits given and equipment used in the following descriptions are examples only and could be varied without departing from the scope of the invention. The operating parameters are entered into the control unit 50 and the analytical procedure is started at the control unit. The operating cycle begins with the supporting electrolyte burette 12 and the sample burette 14 empty.

The measurement cell 10 is full of uncontaminated supporting electrolyte and the sample purge vessel 24 is full of the sample to be analyzed. The operating sequence commences under the control of the unit 50 by opening a valve 91 to cause the cell 10 to be purged with nitrogen supplied on line 43 after passing through the gas wash bottle 34. This operation continues for a period of 165 seconds. At the same time as the purge operation is commenced, the control unit 50 controls the valve 29 to allow supporting electrolyte to flow from the supporting electrolyte reservoir 31 along the line 33, through valve 29 and into the burette 2 via the line 35. The control unit 50 also controls the valve 25 to supply sample electrolyte from the vessel 24 along line 23, through valve 25 and into burette 14 via line 27. The valves 25 and 29 remain in the fill position for a period of 55 seconds to allow the burettes 12 and 14 to be filled with supporting electrolyte and sample electrolyte respectively. Initially the control unit also controls a valve 93 to cause the vessel 24 to be purged with nitrogen which is supplied to the vessel after passing through the gas wash bottle 32. The vessel 24 is purged with nitrogen for a period of 86 seconds. Nitrogen is supplied to the gas wash bottles 32 and 34 via lines 85 and 83 respectively.

After the 55 second time interval has elapsed, the control unit switches the three way valve 25 and three way valve 49 so that the sample burette is emptied to waste via lines 27, 47 and 52. This operation lasts from time 56 seconds to 85 seconds. At time level 86 seconds, the sample burette 14 is again filled after three way valve 25 is adjusted to allow sample electrolyte to flow from the vessel 24 into the burette 14 in the manner described above. This procedure takes place from time 86 seconds to 140 seconds. At time 141 seconds about 15% of the volume of sample burette 14 is dispensed to waste by the control unit 50 controlling the valves 25 and 49 for a period of 19 seconds to allow the sample burette to empty to waste along lines 27, 47 and 52. This operation assists in removing air bubbles from the sample burette and the lines. At time 145 seconds the sample purge vessel 24 is drained by the control unit 50 opening valve 75 so that the contents of the vessel 24 drain through line 73 to waste. This operation lasts for 5 seconds.

At time level 161 seconds 10% of the volume of sample burette 14 is dispensed through the flow nozzle 16 in measurement cell 10 by the control unit 50 controlling valves 25, 49 and 39 so that the sample electrolyte flows along lines 27, 47, 51, and 41 to the flow nozzle 16. This operation lasts until time 185 seconds and is used to flush the lines ready for the experiment to begin.

At time level 165 seconds the sample purge vessel 24 is refilled through line 99 from an external sampling device 95 under the control of the control unit 50. This operation lasts from time 165 seconds to time 220 seconds. At time 190 seconds a fresh mercury drop 150 is dispensed and supported by support 22 after the old drop is dislodged. This operation takes approximately 1 second and is also under the control of the control unit 50 which allows a drop of mercury to flow from a mercury reservoir (not shown) through the support 22.

At time level 200 seconds the control unit 50 controls the deposition potential of the electrode system 79 which comprises a reference electrode 81, an auxiliary electrode 83 and the mercury drop electrode 150 suspended from the support 22. At time level 200 seconds the valves 25, 29 and 39 are again controlled to allow sample electrolyte to flow along the lines 27, 47, 51 and 41 to the nozzle 16 so that a specific volume of sample electrolyte flows into the measurement cell, through the nozzle 16 so that the sample solution is directed onto the mercury drop so that it is enveloped by the sample solution. This operation takes place for 100 seconds up until time limit 300 seconds and enables the accumulation of impurity elements from the sample solution on the mercury drop electrode.

At time level 300 seconds the transient time domain stripping technique commences under the control of the unit 50. The valves 25, 49 and 39 are closed so that no further sample electrolyte flows into the cell 10 and the electrode system is enveloped by supporting electrolyte as the dense sample electrolyte settles in the bottom of cell 10. During the stripping cycle impurities accumulated on the mercury drop electrode are stripped out into the supporting electrolyte in the vessel 10 and their electrochemical responses are measured under the control of the unit 50. This operation continues until time limit 400 seconds.

At time level 400 seconds the data from the experiment is evaluated and a relevant output is provided. The output may be in the form of an alarm if necessary, a process control sequence, a graph or data output. This continues up until time level 480 seconds. At time level 400 seconds the valves 29 and 39 are operated to allow supporting electrolyte from the burette 12 to be dispensed into the cell 10 via the lines 35, 37 and 41. The supporting electrolyte flows into the cell 10 through the nozzle 16 and at time level 480 seconds the control unit 50 controls the valves 29 and 39 to shut off the flow of supporting electrolyte.

The remaining volume of the sample burette 14 is dispensed to waste after the valves 25 and 49 are adjusted by the control unit 50. During the time interval 400 seconds to 425 seconds the sample electrolyte introduced during the experiment and some contaminated supporting electrolyte are drained out of the measurement cell 10 through the outlet 20 by opening the valve 97 under the control of the unit 50 so that the sample electrolyte and supporting electrolyte together with mercury which accumulates in the bottom of the cell 10 are drained into the mercury catch vessel 40. The mercury catch vessel 40 has an outlet 42 and an overflow line 65 which are provided with valves 63 and 67. The valves 63 and 67 may be controlled by the unit 50 to allow the mercury to drain to waste through valve 63 and sample electrolyte and supporting electrolyte to overflow through line 65 to waste.

The sample purge vessel 24 is also provided with an overflow line 69 and a valve 71 which may be controlled by the unit 50 to allow overflow of sample solution from the purge vessel 24.

The cell 10 includes an overflow line 57 to allow supporting electrolyte to flow out of the cell 10 if necessary when supporting electrolyte or sample electrolyte is injected into the cell 10 through the nozzle 16.

At time level 480 seconds the cycle ends and may be recommenced again at any time under the control of the unit 50.

If desired, a solution of known concentration can be introduced to the sample purge vessel 24 from the external sampling device 95 under the control of the control unit 50 for calibration purposes.

The invention will be further illustrated with reference to the following examples.

Results used in the following examples were obtained on a system comprising the following components. A microcomputer controlling sample preparation and presentation to the measurement cell, wave form generation, data acquisition, data evaluation and data reporting. A measurement cell employing a three electrode arrangement, with the hanging mercury drop electrode mode as the working electrode, silver/silver chloride (1 molar potassium chloride) as the reference electrode and platinum or glassy carbon as the auxiliary electrode. A bottom-drained electrochemical cell for matrix exchange during determination unless otherwise stated. A Princeton Applied Research flow injection nozzle as described in U.K. patent specification No. 2017920. Peristaltic pumps and/or burettes for zinc plant and supporting electrolyte addition.

Differential pulse anodic stripping voltammetry with flow injection analysis under stopped flow conditions was used in all examples. The operating parameters for this mode of operation were ramp step, 5 millivolt; pulse height, 50 millivolt and sample solution flow rate, 3.0 milliliter per minute. Pulse time, deposition time, working electrode potential and supporting electrolyte were varied appropriately, and are stated for each example.

EXAMPLE 1

(a) Unattended continual monitoring of cadmium in zinc plant electrolyte (specific gravity=1.35) was conducted over a ten hour period. The neutral zinc sulphate solution contained 120 gram of zinc/liter and 185 microgram of cadmium/liter. The pulse time, deposition time and deposition potential were 5 milliseconds, 60 seconds and $-0.85$ volts versus the reference electrode respectively. The supporting electrolyte used was 1 molar potassium chloride (specific gravity=1.05).

Seventy determinations of cadmium with a measurement cycle of approximate eight minutes, gave an average peak value of 1150 nanoamps and a standard deviation of $\pm 60$ nanoamps, which is equivalent to $185\pm 10$ microgram of of cadmium/liter. This represents an error of 5%. The peak of potential was invariant at $-600\pm 5$ millivolts.

The results were obtained without manual intervention and substantiate the viability of the procedure for the continual monitoring of low concentrations of an impurity, namely cadmium, in a process stream which contains a very much greater concentration of another electrochemically active species, namely zinc.

In this example the matrix exchange involved is from zinc sulphate into 1 molar potassium chloride. An amount of solution equal to the total volume of sample and supporting electrolyte (25 percent of total volume) added during each measurement cycle was drained from the bottom of the cell during each measurement cycle.

(b) The continual monitoring of copper in zinc plant electrolyte was investigated using a conventional top-drained electrochemical cell. The neutral zinc sulphate solution contained 120 gram of zinc/liter and 10 microgram of copper/liter. The pulse time, deposition time and deposition potential were 60 milliseconds, 480 seconds and $-0.40$ volts versus the reference electrode respectively. The supporting electrolyte used was 1 molar potassium chloride. After only 4 consecutive runs, the peak response had decreased from 190 nanoamps to 110 nanoamps and the peak potential had shifted from $-0.20$ volts to $-0.10$ volts versus the reference electrode and was almost totally obscured by an invariant background wave. Without removal of the zinc sulphate sample solution from the base of the cell as previously described, contamination of the supporting electrolyte occurs and the matrix exchange process necessary for accurate determinations is rendered inadequate.

EXAMPLE 2

Determinations of copper and cadmium were conducted in neutral zinc sulphate solution containing 120 gram of zinc/liter and 190 and 95 microgram of cadmium and copper/liter respectively.

The response for copper increased from 144 to 506 nanoamps as the pulse time decreased from 60 to 5 milliseconds. The deposition time and deposition potential were 60 seconds and $-0.40$ volts versus the reference electrode respectively. The supporting electrolyte was 1 molar potassium chloride.

An increase in cadmium response from 1006 to 1962 nanoamps was observed for pulse times of 50 and 5 milliseconds and deposition times of 15 and 10 seconds respectively. The supporting electrolyte was 1 molar potassium chloride and the deposition potential was $-0.85$ volts versus the reference electrode.

For the simultaneous determination of both the above impurities, decreasing the pulse time provided increased sensitivity which enabled more accurate determinations and the possibility of shorter deposition times and hence measurement cycles. The measurement involved a matrix exchange from a zinc sulphate to a potassium chloride medium and was conducted in a bottom-drained cell, which was drained after each measurement cycle. Anodic stripping volammetry could not be used to measure this pair of impurities simultaneously in the sample matrix without exchange into a modified supporting electrolyte.

EXAMPLE 3

The peak potentials for cadmium, thallium, lead, antimony and copper in 1 molar potassium chloride and 1 molar sodium nitrate respectively are as follows: cadmium, $-0.68$ and $-0.63$; thallium, $-0.52$ and $-0.49$; lead, $-0.47$ and $-0.44$; antimony, $-0.20$ and $-0.11$; and copper, $-0.20$ and $-0.01$ volts (all values versus the reference electrode).

In stripping voltammetry great importance is placed on resolution of peaks, to effect accurate determinations, thus well separated peak potentials are required.

The above values show that the preferred supporting electrolyte for copper and antimony determination is a nitrate solution. In 1 molar sodium nitrate a difference of 100 millivolts exists between the two peak potentials. A chloride medium such as 1 molar potassium chloride is preferred for the determination of cadmium, thallium and lead, as a 210 millivolt difference exists between cadmium and lead compared with 190 millivolts in 1 molar sodium nitrate.

However, for many applications it is possible to determine a large set of impurities in a single supporting electrolyte. This is illustrated by the results in Table 2 for the simultaneous determination of cadmium, lead, antimony and copper in a solution containing 120 g zinc/liter. In each case the sample was diluted 50% with water and acidified to pH=4 before measurement. The pulse time was 50 milliseconds and sodium nitrate was the supporting electrolyte.

TABLE 2

Simultaneous Determination of Cadmium, Lead, Antimony and Copper in Zinc Sulphate Solution

| Impurity Measured | Peak Potential volts versus ref. | Sample 1 Concentration microgram/liter | Sample 1 Peak Height nA | Sample 2 Concentration microgram/liter | Sample 2 Peak Height nA |
|---|---|---|---|---|---|
| Cadmium | −0.63 | 100 | 410 | 200 | 815 |
| Lead | −0.44 | 50 | 200 | 150 | 594 |
| Antimony | −0.11 | 100 | 87 | 200 | 170 |
| Copper | −0.01 | 50 | 222 | 130 | 569 |

It would not have been possible to measure all four elements listed in Table 2, using a potassium chloride supporting electrolyte. However, if it was necessary to determine cadmium accurately in the presence of a large excess of lead, the use of a molar potassium chloride supporting electrolyte might be necessary. In such cases, where two different supporting electrolytes are required to determine an extensive set of components in a sample, there are two options:

(i) Change the supporting electrolyte in a single measurement cell between the determinations of sub-sets of components. This step can be carried out automatically according to a pre-programmed sequence.

(ii) Split the sample flow between two measurement cells, operating with different supporting electrolytes.

The disadvantages of the former procedure are relatively long measurement cycles and increased consumption of supporting electrolytes.

For a sample of the type indicated above, 1 molar sodium nitrate is the preferred supporting electrolyte. For many applications, the aforementioned components in the above sample could be adequately determined in a single measurement cycle using this supporting electrolyte.

EXAMPLE 4

Determinations of copper and antimony were made on a continuously flowing process stream in an electrolytic zinc plant. A proprietary automated sampling system was used to sample the process stream at approximately ten minute intervals, dilute the process sample by 50% with water and acidify it to pH=4, before measurement. The deposition potential was −0.425 volts versus the reference electrode, the pulse time in the stripping step was 50 milliseconds and the supporting electrolyte was 1 molar sodium nitrate.

The sampling and measurement systems were operated for a twenty four hour period under microprocessor control without manual intervention.

The process stream contained 120 g zinc/liter and had been purified to remove copper and antimony to low levels. During most of the period of the operation the process plant was normal and the measured copper and antimony levels ranged from between 5 micrograms/liter and 25 micrograms/liter and from between 10 and 25 micrograms/liter respectively.

After 19 hours 26 minutes, abnormally high copper levels were detected in the process stream sample as shown in Table 3. Immediate examination of the process operation, in response to the high levels of copper indicated by the measurement system, showed that the filter medium used to separate a copper rich product immediately ahead of the sampling location had failed. The process fault was rectified and by 20 hours 08 minutes, copper levels had decreased to the normal levels of 25 micrograms/liter. Antimony is not removed by the process step which failed and hence antimony levels measured in the process sample were acceptable at all times, as shown in Table 3. This example illustrates the use of frequent measurements to enable metallurgical processes to be operated more efficiently.

TABLE 3

Long Term Automated Measurement of Copper and Antimony in an Electrolytic Zinc Plant Process Stream

| Time Hours | Time Minutes | Copper Concentration micrograms/liter | Antimony Concentration micrograms/liter |
|---|---|---|---|
| 19 | 05 | 11 | 17 |
| 19 | 15 | 20 | 18 |
| 19 | 26 | 165 | 29 |
| 19 | 36 | 85 | 24 |
| 19 | 47 | 49 | 18 |
| 19 | 58 | 31 | 20 |
| 20 | 08 | 23 | 18 |
| 20 | 19 | 19 | 18 |

The method and apparatus of the present invention can determine the concentration of impurity components such as copper, cadmium, lead, antimony, nickel, cobalt, thallium, arsenic, tin and germanium in sulphate solutions suitable for zinc recovery by electrolysis in which impurity concentrations may be as low as $10^{-9}$ times the concentration of zinc. In the case of zinc sulphate electrolytes the ratio of an impurity concentration to the host zinc concentration is often of the order of 1 to $10^7$ in the purified electrolyte, compared with the ratios as low as 1 to 10 in unpurified electrolyte. Previously there has been no known method of determining, without manual intervention, the concentrations of impurities in process streams sampled sequentially from locations entering and leaving a purification step involving such massive changes in impurity concentration.

It should be understood that the present invention is not limited to solutions suitable for zinc electrowinning and can be applied for determining electrochemically active components in a sample in general.

Although the preferred embodiment of the invention has been described with reference to the cell shown in the drawings, the invention could be carried out in a conventional cell, which overflows from the top, the more dense sample flows by gravity to the base of the cell where it accumulates. This type of cell is referred to as a top-drained cell. Thus after a small number of automated measurements, mixing occurs and the supporting electrolyte becomes substantially contaminated by the sample matrix. This contamination changes the sensitivity of the measurements obtained when the deposited impurities are stripped from the mercury drop into the supporting electrolyte. Under these circumstances the exchange of impurities from the sample matrix to the supporting electrolyte matrix is inefficient.

In another, but less preferred embodiment, the sample and supporting electrolyte are flushed from the cell after either each measurement cycle or after a small number, typically less than 5, of measurement cycles and supporting electrolyte is completely replaced before the next measurement cycle. This mode of automated operation is achieved either by flushing out a top drained conventional cell with supporting electrolyte, or by draining and then refilling a bottom drained cell, in which only partial replacement of the supporting electrolyte normally occurs.

However, in some instances there may be an advantage in changing the supporting electrolyte matrix between the sequential measurement of two different impurities. Under these circumstances the complete replacement of the supporting electrolyte between measurement cycles will be justified.

Since modifications within the spirit and scope of the invention may readily be effected by persons skilled within the art, it is to be understood that this invention is not limited to the particular embodiment described by way of example hereinabove.

The claims defining the invention are as follows:

1. A method for the determination of electrochemically active components in a process stream comprising the steps of immersing a working electrode in a supporting electrolyte, injecting a flow of a sample solution of the stream containing an electrochemically active component onto said working electrode so that the electrode is now surrounded with the sample solution to deposit said component onto the working electrode, said supporting electrolyte being less dense than said sample solution, stopping the flow of injected sample solution so that the sample solution sinks away from the working electrode to leave the working electrode having the component deposited thereon again immersed in the supporting electrolyte to thereby effect a matrix exchange, stripping the deposited component from the working electrode into the supporting electrolyte and determining the presence of the component in the supporting electrolyte.

2. The method of claim 1 wherein the presence of the component is determined by measuring its electrochemical response in the supporting electrolyte.

3. The method of claim 1 wherein the working electrode is a mercury electrode.

4. A method for the determination of impurities in an electrolyte containing a much higher concentration of another electrochemically active species characterized by the automated and continual performance of a series of sequential steps which are repeated under microprocessor control, said sequence of steps comprising depositing said impurities from an injected flow of an electrolyte sample containing the impurities onto a mercury electrode immersed in a supporting electrolyte which is less dense than the sample electrolyte, stopping the flow of injected sample electrolyte and finally effecting a matrix exchange by stripping the deposited impurities from the mercury electrode into the less dense supporting electrolyte using variable time domain transient electrochemical stripping voltammetry and determining the presence of the impurities in the supporting electrolyte.

5. The method of claim 4 further including the step of removing excess of said another electrochemically active species prior to the sample electrolyte containing that species being injected onto said mercury electrode.

6. The method of claim 4 wherein the method takes place in a measurement cell which includes said mercury electrode, a flow injecting nozzle for injecting a flow of the sample electrolyte onto the mercury electrode, an outlet arranged at the bottom of the cell for removing sample electrolyte from said cell and means for introducing supporting electrolyte into said cell whereby when the flow of sample electrolyte is stopped, sample electrolyte sinks to the bottom of the cell and is removed from the cell via the outlet.

7. The method of claim 4 wherein the variable time domain transient electrochemical stripping voltammetry is differential pulse anodic stripping voltammetry having a pulse time which is in the range of 1 to 400 milliseconds or linear sweep stripping voltammetry.

8. The method of claim 4 wherein the impurities comprise one or more of the group of elements consisting of cadmium, copper, lead, antimony, thallium, nickel, cobalt, arsenic, tin and germanium and the electrochemically active species present at a much higher concentration is zinc, and the electrolyte is a zinc sulphate electrolyte.

9. The method of claim 4 wherein the supporting electrolyte comprises a chloride solution.

10. The method of claim 9 wherein the chloride solution was a concentration on the range 0.1 to 4.0 molar.

11. The method of claim 4 wherein the supporting electrolyte comprises a nitrate solution.

12. The method of claim 11 wherein when copper and antimony are simultaneously present as impurities the supporting electrolyte is a nitrate solution having a concentration in the range 0.1 to 4.0 molar.

13. The method of claim 4, wherein for determining the impurity set cadmium, copper, lead, antimony and thallium a first measurement cycle is made with a chloride supporting electrolyte and the components cadmium, lead and thallium are determined during the stripping step followed by a second measurement cycle in which the supporting electrolyte is a nitrate solution and the components copper and antimony are determined during the stripping step.

14. An apparatus for the determination of impurities in an electrolyte containing a much higher concentration of another electrochemically active species comprising a measurement cell for holding a supporting electrolyte, means for forming a mercury electrode to be immersed in said supporting electrolyte, means for injecting a flow of a sample of the electrolyte containing said impurities onto said mercury electrode, said means for injecting the flow of sample electrolyte including a flow nozzle arranged adjacent to said mercury electrode when said mercury electrode is formed, said flow nozzle injecting the sample electrolyte towards the mercury electrode so that the sample electrolyte displaces said supporting electrolyte surrounding the mercury electrode so that the mercury electrode is surrounded by the sample electrolyte whilst both said sample electrolyte and said mercury electrode are within the supporting electrolyte, means for energizing said mercury electrode to cause said impurities to be deposited thereon, means for stopping the injection of the sample electrolyte from the flow nozzle so that the sample electrolyte moves away from said mercury electrode to leave the mercury electrode surrounded by the supporting electrolyte to thereby effect a matrix exchange, means for again energizing said mercury electrode so as to strip deposited impurities from the mercury electrode into the supporting electrolyte using variable time domain transient electrochemical stripping voltammetry and microprocessor control means for automating in sequence the injecting means, the stopping means and the energizing means.

* * * * *

UNITED STATES PATENT AND TRADEMARK OFFICE
CERTIFICATE OF CORRECTION

PATENT NO.  : 4,804,443

DATED       : February 14, 1989

INVENTOR(S) : Oliver M.G. Newman, Alan M. Bond, and Roger W. Knight

It is certified that error appears in the above-identified patent and that said Letters Patent is hereby corrected as shown below:

On the title page, item 75, "Robert W. Knight" should read
--Roger W. Knight--.

Signed and Sealed this

Sixth Day of February, 1990

*Attest:*

JEFFREY M. SAMUELS

*Attesting Officer*   *Acting Commissioner of Patents and Trademarks*